(12) United States Patent
Germann et al.

(10) Patent No.: US 6,656,937 B2
(45) Date of Patent: Dec. 2, 2003

(54) SUBSTITUTED GLUTARIMIDES AND THEIR USE AS INHIBITORS OF IL-12 PRODUCTION

(75) Inventors: Tieno Germann, Herzogenrath (DE); Stefanie Frosch, Aachen (DE); Erik Wade, Aachen (DE); Helmut Buschmann, Aachen (DE); Oswald Zimmer, Wuerselen (DE)

(73) Assignee: Gruenenthal, GmbH, Aachen (DE)

( * ) Notice: Subject to any disclaimer, the term of this patent is extended or adjusted under 35 U.S.C. 154(b) by 0 days.

(21) Appl. No.: 10/198,073

(22) Filed: Jul. 19, 2002

(65) Prior Publication Data

US 2003/0064987 A1 Apr. 3, 2003

Related U.S. Application Data

(63) Continuation-in-part of application No. PCT/EP01/00155, filed on Jan. 9, 2001.

(30) Foreign Application Priority Data

Jan. 21, 2000 (DE) .......................................... 100 02 509

(51) Int. Cl.⁷ .................. A61K 31/5355; A61K 31/451; A61K 31/454; C07D 211/12; C07D 211/56; C07D 295/102
(52) U.S. Cl. ................................ 514/231.5; 514/237.2; 514/326; 514/328; 546/207; 546/208; 546/219; 544/111; 544/129
(58) Field of Search ................................ 546/208, 219, 546/207; 514/231.5, 237.2, 326, 328; 544/111, 129

(56) References Cited

U.S. PATENT DOCUMENTS

| 2,673,205 | A | | 3/1954 | Hoffmann et al. |
| 3,214,431 | A | * | 10/1965 | Kopaka Rao et al. ...... 546/219 |
| 5,114,937 | A | | 5/1992 | Hamby et al. |
| 5,300,516 | A | | 4/1994 | Mackenzie et al. |
| 6,008,360 | A | | 12/1999 | Camus et al. |
| 6,316,471 | B1 | * | 11/2001 | Muller et al. ................ 514/323 |

FOREIGN PATENT DOCUMENTS

| EP | 0856513 | 8/1998 |
| EP | 0989121 | 3/2000 |

OTHER PUBLICATIONS

Chemical Abstracts, vol. 119, 1993, p. 924.
David R. Moller, et al., "Inhibition of IL-12 Production by Thalidomide" The Journal of Immunology, 1997, pp. 5157–5161.

Giorgio Trinchieri, "Interleukin–12: A Proinflammatory Cytokine with Immunoregulatory Functions that Bridge Innate Resistance and Antigen–Specific Adaptive Immunity" Annual Review Immunol., vol. 13, 1995, pp. 251–276.
Sylvie Trembleau, et al., "The role of IL–12 in the induction of organ–specific autoimmune diseases" Immunology Today, vol. 16, No. 8, 1995, pp. 383–386.
Gabriele Mueller, et al., "IL–12 as Mediator and Adjuvant for the Induction of Contact Sensitivity In Vivo" American Association of Immunologist, 1995.
Markus F. Neurath, et al., "Antibodies to Intereleukin 12 Abrogate Established Experimental Colitis in Mice" Journal of Experimental Medicine, vol. 182, 1995, pp. 1281–1290.
Benjamin M. Segal, et al., "An Interleukin (IL)–10/IL–12 Immunoregulatory Circuit Controls Susceptibility to Autoimmune Disease" Journal of Experimental Medicine, vol. 187, No. 4, 1998, pp. 537–546.
Fiona Powrie, "T Cells in Inflammatory Bowel Disease: Protective and Pathogenic Roles" Immunity, vol. 3, 1995, pp. 171–174.
Angelika Rudolphi, et al, "Polyclonal expansion of adoptively transferred CD4+ alpha beta T Cells in the colonic lamina propria of scid mice with colitis" Eur. J. Immunol., vol. 26, 1996, pp. 1156–1163.
Soren Bregenholt, "Increased intracellular TH1 cytokines in scid mice with inflammatory bowel disease" Eur. J. Immunol., 1998, pp. 379–389.
Mario Clerici, et al., "Type 1/type 2 cytokine modulation of T–cell programmed cell death as a model for human immunodeficiency virus pathogenesis" Proc. Natl. Acad. Sci., vol. 91, 1994, pp. 11811–11815.
Jerome Estaquier, et al., "T Helper Type1/T Helper Type 2 Cyokines and T Cell Death: Preventive Effect of Interleukine 12 on Activation–induced and CD95 (FAS/APO–1)–mediated Apoptosis of CD4+T Cells from Human Immunodeficiency Virus–infected Person" J. Exp. Med., vol. 182, 1995, pp. 1759–1767.

* cited by examiner

*Primary Examiner*—Rita Desai
(74) *Attorney, Agent, or Firm*—Crowell & Moring LLP

(57) ABSTRACT

Substituted glutarimides of formula I

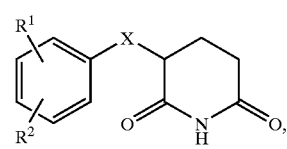

and their method of making. Also disclosed are pharmaceutical compositions comprising the glutarimidie, particularly as immunomodulators and as inhibitors of angiopathies, or haematological or oncological diseases, as well as a method for treating various diseases using the glutarimides.

13 Claims, No Drawings

SUBSTITUTED GLUTARIMIDES AND THEIR USE AS INHIBITORS OF IL-12 PRODUCTION

CROSS REFERENCE TO RELATED APPLICATIONS

The present application is a continuation-in-part of international patent application no. PCT/EP01/00155, filed Jan. 9, 2001, designating the United States of America, the entire disclosure of which is incorporated herein by reference. Priority is claimed based on Federal Republic of Germany patent application no. 100 02 509.9, filed Jan. 21, 2000.

FIELD OF THE INVENTION

The invention concerns substituted glutarimides having the general formula I

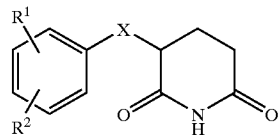

their production and their use in medicaments.

BACKGROUND OF THE INVENTION

Autoimmune diseases arise as a result of a reactivity of the immune system against structures or components occurring naturally in the body. As part of this process, the normally existing tolerance towards the body's own tissue lapses. In addition to antibodies, T-lymphocytes and monocytes/macrophages in particular play a significant role in the pathogenesis of the various autoimmune diseases. Activated monocytes and/or macrophages secrete a number of different proinflammatory mediators that are directly or indirectly responsible for destroying the tissue affected by the autoimmune disease. The activation of monocytes/macrophages occurs either in the interaction with T-lymphocytes or via bacterial products such as lipopolysaccharide (LPS).

IL-12 is a heterodimeric molecule consisting of a covalently bonded p35 and p40 chain. The molecule is formed by antigen-presenting cells (monocytes/macrophages, dendritic cells, B-lymphocytes). The formation of 1L-12 by monocytes/macrophages is triggered either by various microbial products such as LPS, lipopeptides, bacterial DNA or in the interaction with activated T-lymphocytes (Trinchieri, 1995, Ann. Rev. Immunol. 13: 251). IL-12 has a central immunoregulatory significance and is responsible for the development of proinflammatory TH1 reactivities. The presence of a TH1 immune reaction against self-antigens leads to the occurrence of serious diseases.

The significance of inflammatory cytokines such as IL-12 for the development and course of inflammations and autoimmune diseases has been clearly documented by numerous animal experimental and preliminary clinical trials. The pathophysiological importance of IL-12 has been demonstrated in various animal models for diseases such as rheumatoid arthritis, multiple sclerosis, diabetes mellitus and inflammatory diseases of the intestines, skin and mucous membranes (Trembleau et al., 1995, Immunol. Today 16: 383; Muller et al., 1995, J. Immunol. 155: 4661; Neurath et al., 1995, J. Exp. Med. 182: 1281; Segal et al., 1998, J. Exp. Med. 187: 537; Powrie et al., 1995, Immunity 3: 171; Rudolphi et al., 1996, Eur. J. Immunol. 26: 1156; Bregenholt et al., 1998, Eur. J. Immunol. 28: 379). Application of IL-12 could trigger the relevant disease and neutralisation of endogenous IL-12 led to the course of the disease being moderated, or even the cure of the animals. The use of antibodies against IL-12 in humans is imminent.

It can be said in summary that an excess of IL-12 conditions the pathophysiology of a number of inflammatory diseases. Attempts to normalize the IL-12 level therefore have great therapeutic potential.

IL-12 is also involved in regulating the survival of cells. Uncontrolled cell growth is regulated by apoptosis (programmed cell death) amongst other things. Using T-lymphocytes it has been shown that IL-12 has an anti-apoptotic action and promotes the survival of T-cells (Clerici et al., 1994, Proc. Natl. Acad. Sci. USA 91: 11811; Estaquier et al., 1995, J. Exp. Med. 182: 1759). A local overproduction of IL-12 can therefore contribute to the survival of tumour cells.

Inhibitors of IL-12 formation therefore possess great therapeutic potential.

One potential inhibitor of IL-12 formation is the known active agent thalidomide (Journal of Immunology 159 (10), 5157–5161 (1997)).

U.S. Pat. No. 5,114,937 describes renin-inhibiting peptide derivatives, the carboxamide groups in which are replaced by their isosteres. The compounds are suitable for the treatment of renin-associated hypertension, congestive heart failure, hyperaldosteronism, glaucoma and diseases caused by the retroviruses HTLV-I, -II and -III.

DE 198 43 793 describes substituted benzamides with immunomodulatory properties in which the ring-containing structural parts of the molecule are linked together by an amide bond. The disadvantage of the amide bond is its susceptibility to hydrolysis with an accompanying loss of action for the compound.

The object of the invention was therefore to develop new immunomodulators that are suitable for the treatment and/or prophylaxis of diseases caused by formation of the proinflammatory cytokine IL-12 and that at the same time display an improved hydrolytic stability.

DETAILED DESCRIPTION OF THE INVENTION

It has now been discovered that substituted glutarimides satisfy the above requirements.

The invention accordingly provides substituted glutarimides having the formula I

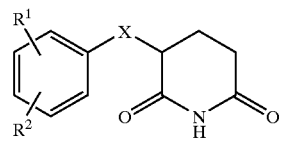

in which X denotes a group having the formula $CH_2$—NH or S—$CH_2$, $R^1$ stands for a carboxyl group; an ester group having the formula $COOR^5$ in which $R^5$ denotes an alkyl group (straight-chain or branched) with 1 to 6 carbon atoms or a benzyl radical; or an amide group having the formula $CONR^6R^7$, in which $R^6$ and $R^7$ are the same or different and represent hydrogen, an alkyl group (straight-chain or branched) with 1 to 6 Carbon atems (optionally substituted with the radical COOR$^5$ and/or a phenyl group), a phenyl radical or taken together with the N atom represent a hydrazide group, a pyrrolidine, piperidine or morpholine ring or stand for an amino group substituted with the radical CH(=O) or COR$^5$, in which R$^5$ is as defined above, and R$^2$ stands for hydrogen, an amino or nitro group, and enantiomers, mixtures of enantiomers, racemates, diastereomers or mixtures of diastereomers thereof in the form of their bases or salts with physiologically compatible acids.

The following substituted glutarimides are particularly preferred:

2-[(3S)-(2,6-dioxopiperidin-3-ylamino)methyl]benzoic acid,
2-[(3R)-(2,6-dioxopiperidin-3-ylamino)methyl]benzoic acid,
2-[(3S)-(2,6-dioxopiperidin-3-ylamino)methyl]-N,N-diethylbenzamide,
(3S)-[2-morpholine-4-carbonyl)benzylamino]piperidine-2,6-dione,
{2-[(3S)-(2,6-dioxopiperidin-3-ylamino)methyl]benzoylamino}methyl acetate,
2-[(3S)-(2,6-dioxopiperidin-3-ylamino)methyl]benzamide,
2-[(3S)-(2,6-dioxopiperidin-3-ylamino)methyl]-N-ethyl benzamide,
(3S)-[2-pyrrolidine-1-carbonyl)benzylamino]piperidine-2,6-dione,
2-[(3S)-(2,6-dioxopiperidin-3-ylamino)methyl]benzoic acid hydrazide,
2-[(3S)-(2,6-dioxopiperidin-3-ylamino)methyl]-N-phenyl benzamide,
2-[(3R)-(2,6-dioxopiperidin-3-ylamino)methyl]-N-phenyl benzamide,
2-[(3R)-(2,6-dioxopiperidin-3-ylamino)methyl]-N,N-diethyl benzamide,
2-[(3R)-(2,6-dioxopiperidin-3-ylamino)methyl]benzamide,
2-[(3S)-(2,6-dioxopiperidin-3-ylamino)methyl]methyl benzoate,
2-[(3S)-(2,6-dioxopiperidin-3-ylamino)methyl]benzyl benzoate,
2-(2,6-dioxopiperidin-3-yl methyl sulfanyl) methyl benzoate,
N-{2-[2,6-dioxopiperidin-3-ylamino)methyl]phenyl}acetamide,
N-{2-[2,6-dioxopiperidin-3-ylamino)methyl]phenyl}formamide,
3-(2,6-dioxopiperidin-3-yl methyl sulfanyl)-6-nitro methylbenzoate, and
2-amino-5-(2,6-dioxopiperidin-3-yl methyl sulfanyl) methyl benzoate.

The present invention also provides methods for the production of compounds according to the invention having the general formula I.

Compounds having the general formula I can be obtained by cyclizing glutaric acid derivatives having the general formula II,

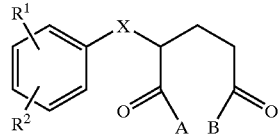

II in which X, R$^1$ and R$^2$ have the same meaning as defined above for formula I, A stands for OH, B for NH$_2$ or NHOH,
or vice versa, in the presence of activating reagents such as carbonyl diimidazole. If X in the compound having the formula I denotes a CH$_2$—NH group, cyclization is preferably performed with compounds having the formula II, in which the NH function is present in protected form, for example with a benzyl oxycarbonyl group, which is then removed at a temperature of between 20 and 40 °C., e.g. with a solution of hydrogen bromide in acetic acid.

Heating a compound of formula II in which A and B both stand for OH in acetic anhydride, first produces a cyclization to the cyclic anhydride, from which the compound having formula I is obtained by heating with urea or another nitrogen source.

Compounds having the general formula I can also be produced from lactams having the general formula III,

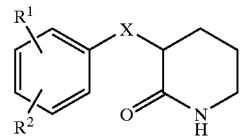

III in which R$^1$, R$^2$ and X have the same meanings as defined above for formula I, by oxidizing compound III to an imide, preferably with m-chloroperbenzoic acid or ruthenium(IV) oxide/sodium periodate.

Compounds having the formula I, in which X stands for the CH$_2$—NH group, can also be obtained by alkylating α-aminoglutarimides having the general formula IV,

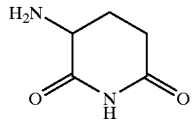

IV with compounds having the general formula V,

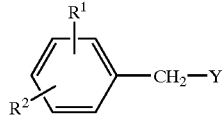

V in which R$^1$ and R$^2$ have the same meanings as above and Y stands for a chlorine, bromine or iodine atom or a toluene-4-sulfonate radical.

Compounds in which X stands for the CH$_2$—NH group can also be obtained by reductive amination from compounds having the general formulae VI and IV, in which R$^1$ and R$^2$ have the same meanings as above.

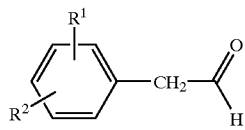

VI

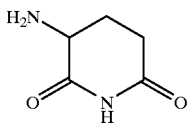

Sodium borohydride, sodium triacetoxyborohydride, sodium cyanoborohydride, the borane-pyridine complex or catalytically excited hydrogen is preferably used as the reducing agent.

Compounds having the formula I where X is $CH_2$—NH can also be obtained by alkylating a compound having the general formula VII,

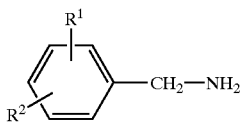

in which $R^1$ and $R^2$ have the same meanings as above, with α-bromoglutarimide having the general formula VIII

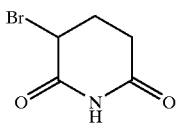

Compounds having the general formula I, in which X stands for an S—$CH_2$ group, can be obtained by adding a mercaptan having the general formula X

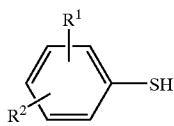

to 3-methylene glutarimide having the general formula IX

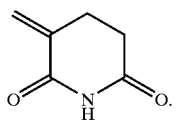

The reaction is preferably performed in solvents such as acetonitrile or toluene with addition of tertiary amines such as triethylamine or diisopropyl ethylamine at temperatures of 80 to 110° C.

Compounds having the formula I, in which $R^2$ stands for an amino group, can generally be obtained by reduction of compounds having the formula I where $R^2$=$NO_2$. The reduction is performed, for example, by catalytically excited hydrogen in acid-containing organic solvents such as ethyl acetate, whereby palladium catalysts are preferably used. Alternatively, the reduction can be performed with metals such as tin or iron in acid solution.

The compounds according to the invention possess immunomodulatory activity which is demonstrated by an inhibition of the production of IL-12 by LPS-activated monocytes. In comparison to compounds that have already been proposed, they also demonstrate an improved hydrolytic stability. They are suitable for the treatment and/or prophylaxis of inflammation and autoimmune diseases and also of haematological/oncological diseases.

Accordingly, the present invention also includes methods and pharmaceutical compositions for the treatment of these diseases. The method according to the invention comprises administering to a mammal, such as a human, in need thereof, an effective amount of a suitable pharmaceutical composition comprising a substituted glutarimide of the invention.

The above groups of diseases include, amongst others, inflammations of the skin (e.g. atopic dermatitis, psoriasis, eczema), inflammations of the respiratory tracts (e.g. bronchitis, pneumonia, bronchial asthma, ARDS (adult respiratory distress syndrome), sarcoidosis, silicosis/fibrosis), inflammations of the gastrointestinal tract (e.g. gastroduodenal ulcers, Crohn's disease, ulcerative colitis), and diseases such as hepatitis, pancreatitis, appendicitis, peritonitis, nephritis, aphthosis, conjunctivitis, keratitis, uveitis, and rhinitis.

The autoimmune diseases include, for example, arthritic diseases (e.g. rheumatoid arthritis, HLA-B27-associated diseases), Behcet's disease, and multiple sclerosis, juvenile diabetes or lupus erythematosus.

Further indications are sepsis, bacterial meningitis, cachexia, transplant rejection reactions, graft-versus-host reactions as well as reperfusion syndrome and atherosclerosis along with angiopathies (such as macula degeneration, diabetic retinopathies).

The symptoms that can be inhibited by a reduction in IL-12 also include haematological diseases such as multiple myeloma and leukaemias, along with other oncological diseases such as glioblastoma, prostate cancer and mammary cancer.

Medicaments according to the invention contain, in addition to at least one compound having the general formula I, carriers, fillers, solvents, diluents, dyestuffs and/or binders. The choice of auxiliaries and the quantities to be used depend on whether the medicament is to be administered by oral, rectal, ophthalmic (intravitreal, intracameral), nasal, topical (including buccal and sublingual), vaginal or parenteral (including subcutaneous, intramuscular, intravenous, intradermal, intratracheal and epidural) means.

Preparations in the form of tablets, chewable tablets, sugar-coated tablets, capsules, granules, drops, liquids or syrups are suitable for oral administration, while solutions, suspensions, easily reconstituted dry preparations and sprays are suitable for administration by parenteral or topical means or by inhalation. Cutaneous administration forms are salves, gels, creams and pastes. Ophthalmic administration forms include drops, salves and gels. Compounds according to the invention contained in a reservoir in dissolved form, a carrier film or a plaster, optionally with the addition of skin-penetrating agents, are examples of suitable percutaneous administration forms. The compounds according to the invention can be released on a delayed basis from oral or percutaneous forms of preparation.

The amount of active agent to be administered to patients varies according to the weight of the patient, the type of administration, the indication and the severity of the disease. 1 to 150 mg/kg of at least one compound according to the invention having the formula I are conventionally administered.

EXAMPLES

The following examples serve to describe the present invention in greater detail, and should not be construed to limit the invention in any way.

Silica gel 60 (0.040–0.063 mm) from E. Merck, Darmstadt, was used as stationary phase for the chromatographic separations. The mixing ratios of the eluents are always given as percentages by volume.

The substances were characterised by their melting point and/or the $^1$H-NMR spectrum. The spectra were recorded at 300 MHz using a Gemini 300 device from Varian. The chemical shifts are given in ppm (δ-scale). Tetramethyl silane (TMS) was used as internal standard.

Example 1

3-(2-chlorobenzylamino) piperidine-2,6-dione; hydrochloride

Step 1:

3-bromopiperidine-2,6-dione 4.5 ml bromine were added to 10.2 g glutarimide suspended in 20 ml chloroform and the mixture was stirred in a closed vessel for 90 minutes at a bath temperature of 110° C. After cooling, the vessel was opened and stirring was continued until no more hydrogen bromide escaped. The reaction mixture was evaporated in vacuo, the residue dissolved in ethanol and evaporated again. 17.1 g (99% of theoretical) of the title compound remained in the form of practically white crystals, which melted at 76 to 83° C.

Step 2:

3-(2-chlorobenzylamino) piperidine-2,6-dione; hydrochloride

A solution of 0.39 g of the product from step 1 and 0.71 g 2-chlorobenzylamine in 8 ml N,N-dimethylformamide was stirred for 36 hours at 20° C. After evaporation in vacuo the oily residue was dissolved in 25 ml methanol and the solution stirred for two hours with 1 g Amberlyst A-21. It was filtered, 2 g silica gel were added to the filtrate and it was evaporated until dry. The adsorbed substance was placed in a chromatography column and the product was eluted with a mixture of ethyl acetate/cyclohexane (1/2>1/1) containing 1% triethylamine. The residue remaining after evaporation of the product fractions was dissolved in 10 ml methanol and 25 ml each of diethyl ether saturated with hydrogen chloride and diethyl ether were added to the solution. The precipitated hydrochloride was separated off and recrystallised from methanol/diethyl ether. 0.24 g (41% of theoretical) of the title compound were obtained in the form of crystals, which melted at 217° C. with decomposition.

$^1$H-NMR (DMSO-d$_6$): 2.15–2.34 (1H, m); 2.40–2.56 (1H, m); 2.60–2.80 (2H, m); 4.35 (1H, t, J=13.5 Hz); 4.45 (2H, d, J=13.8 Hz); 7.40–7.94 (4H, m).

Example 2

Using the procedure described in Example 1, step 2 and the corresponding benzylamines, the following compounds were obtained in the same way:

2.1: 3-(2-trifluoromethyl benzylamino) piperidine-2,6-dione; hydrochloride
Melting point: >250° C. (decomposition)

2.2: 3-(2,4-dimethoxybenzylamino) piperidine-2,6-dione; hydrochloride
Melting point: 214° C. (decomposition)

2.3: 3-(2,6-difluorobenzylamino) piperidine-2,6-dione; hydrochloride
Melting point: 208–215° C. (decomposition)

2.4: 3-(2,5-difluorobenzylamino) piperidine-2,6-dione; hydrochloride
Melting point: 208° C. (decomposition)

2.5: 3-(3,5-difluorobenzylamino) piperidine-2,6-dione; hydrochloride
Melting point: 230–236° C. (decomposition)

2.6: 3-[(naphth-1-ylmethyl)amino]piperidine-2,6-dione; hydrochloride
Melting point: 188° C. (decomposition)

2.7: 3-(2,3-difluorobenzylamino) piperidine-2,6-dione; hydrochloride
Melting point: 206–212° C. (decomposition)

2.8: 3-(4-dimethylaminobenzylamino) piperidine-2,6-dione; base 2.9: 3-(4-nitrobenzylamino) piperidine-2,6-dione; hydrochloride 2.10: 3-(3-trifluoromethylbenzylamino) piperidine-2,6-dione; hydrochloride 2.11: 3-(3-trifluoromethoxybenzylamino) piperidine-2,6-dione; hydrochloride
Melting point: 199–201° C.

2.12: 3-[(naphth-2-ylmethyl)amino]piperidine-2,6-dione, base
Melting point: 120–125° C. (decomposition)

2.13: 3-(2-chloro-4-fluorobenzylamino) piperidine-2,6-dione; hydrochloride
Melting point: 241–242° C.

2.14: 3-(3-nitrobenzylamino) piperidine-2,6-dione; hydrochloride
Melting point: from 240° C. with decomposition 2.15: 3-(2-chloro-6-methylbenzylamino) piperidine-2,6-dione; hydrochloride
Melting point: 238–240° C.

2.16: 3-(2-methylbenzylamino) piperidine-2,6-dione; hydrochloride
Melting point: 235–240° C.

2.17: 3-(3,5-dichlorobenzylamino) piperidine-2,6-dione; hydrochloride
Melting point: 234–238° C.

2.18: 3-[3-fluoro-5-(trifluoromethyl) benzylamino] piperidine-2,6-dione; hydrochloride
Melting point: 241–243° C.

2.19: 3-(3-fluorobenzylamino) piperidine-2,6-dione; hydrochloride
Melting point: 231–235° C.

2.20: 3-(3-methylbenzylamino) piperidine-2,6-dione; hydrochloride
Melting point: 240–242° C.

2.21: 3-(4-trifluoromethylbenzylamino) piperidine-2,6-dione; hydrochloride
Melting point: 252–255° C.

2.22: 3-[4-fluoro-2-(trifluoromethyl) benzylamino] piperidine-2,6-dione; hydrochloride
Melting point: from 241° C. with decomposition 2.23: 3-(4-fluorobenzylamino) piperidine-2,6-dione; hydrochloride
Melting point: 241–242° C.

2.24: 3-(4-tert-butylbenzylamino) piperidine-2,6-dione; hydrochloride
Melting point: from 239° C. with decomposition 2.25: 3-(3,5-dimethylbenzylamino) piperidine-2,6-dione; hydrochloride
Melting point: from 226° C. with decomposition 2.26: 3-(3-chlorobenzylamino) piperidine-2,6-dione; hydrochloride
Melting point: 237–238° C.

2.27: 3-(4-methoxybenzylamino) piperidine-2,6-dione; hydrochloride
Melting point: from 227° C. with decomposition 2.28: 3-(2,4-dichlorobenzylamino) piperidine-2,6-dione; hydrochloride
Melting point: 240–242° C.
2.29: 3-(2-fluorobenzylamino) piperidine-2,6-dione; hydrochloride
Melting point: 245–247° C.
2.30: 3-(2-bromobenzylamino) piperidine-2,6-dione; hydrochloride
Melting point: 244–246° C.
2.31: 3-[2-fluoro-5-(trifluoromethyl) benzylamino] piperidine-2,6-dione; hydrochloride
Melting point: from 251° C. with decomposition
2.32: 3-(2,3-dichlorobenzylamino) piperidine-2,6-dione; hydrochloride
Melting point: 246–248° C.
2.33: 3-(3,4-dichlorobenzylamino) piperidine-2,6-dione; hydrochloride
Melting point: 252–254° C.
2.34: 3-[3,5-bis(trifluoromethyl) benzylamino]piperidine-2,6-dione; hydrochloride
Melting point: 263–265° C.
2.35: 3-(3-bromobenzylamino) piperidine-2,6-dione; hydrochloride
Melting point: 229–232° C.
2.36: 3-(4-trifluoromethoxybenzylamino) piperidine-2,6-dione; hydrochloride
Melting point: 253–255° C.
2.37: 3-(4-chlorobenzylamino) piperidine-2,6-dione; hydrochloride
Melting point: 262–265° C.
2.38: 3-(4-methylbenzylamino) piperidine-2,6-dione; hydrochloride
Melting point: 256° C. with decomposition
2.39: 3-(2-ethoxybenzylamino) piperidine-2,6-dione; hydrochloride
Melting point: 208–212° C.
2.40: 3-(2,5-dichlorobenzylamino) piperidine-2,6-dione; hydrochloride
Melting point: 242–246° C.
2.41: 3-(3-methoxybenzylamino) piperidine-2,6-dione; hydrochloride
Melting point: 217–219° C.
All compounds listed under 2.1 to 2.41 are in the form of the racemate.

Example 3

3-(3-aminobenzylamino) piperidine-2,6-dione; hydrochloride 0.56 g of the product from example 2.14 in a mixture consisting of 17 ml ethyl acetate and 0.85 ml 6N hydrochloric acid were hydrogenated at 20° C. under a pressure of 4 bar over 0.17 g palladium on activated carbon (10% Pd). After consumption of the theoretical amount of hydrogen, the mixture was filtered off from the catalyst and the filtrate evaporated in vacuo. After recrystallisation of the residue from methanol, 0.25 g (50% of theoretical) of the racemic title compound were obtained in the form of slightly colored crystals, which melted at 236–239° C.

$^1$H-NMR (DMSO-d$_6$): 2.05–2.20 (m, 1H); 2.28–2.39 (m, 1H); 2.55–2.74 (m, 2H); 3.97–4.12 (q, 2H); 4.18–4.28 (m, 1H); 6.58–6.70 (m, 3H); 7.02–7.11 (m, 1H).

Example 4

Using the procedure described in Example 1, step 2 and the corresponding arylalkylamines, the following compounds were obtained in the same way:

4.1: 3-phenethylaminopiperidine-2,6-dione; hydrochloride
Melting point: from 220° C. with decomposition
4.2: 3-[2-(2-chlorophenyl) ethylaminopiperidine-2,6-dione; hydrochloride
Melting point: 230° C. (decomposition)
4.3: 3-(4-phenylbutylamino) piperidine-2,6-dione; hydrochloride
Melting point: from 231° C. with decomposition
4.4: 3-(N-benzyl-N-methylamino) piperidine-2,6-dione; base
Melting point: 95–115° C.
4.5: 3-(methylnaphth-1-yl methylamino) piperidine-2,6-dione; base
Melting point: 157–162° C.
All compounds listed under 4.1 to 4.5 are in racemic form.
4.6: (2S)-[(3S) or (3R)-(2,6-dioxopiperidin-3-ylamino)] methyl phenylacetate; hydrochloride
Melting point: 200–207° C.
4.7: (2R)-[(3S) or (3R)-(2,6-dioxopiperidin-3-ylamino)] methyl phenylacetate; hydrochloride
Melting point: 171–177° C. (decomposition)
4.8: (2S)-[(3R,S)-(2,6-dioxopiperidin-3-ylamino)]-3-methyl phenylpropionate; hydrochloride
(mixture of diastereomers)
Melting point: 146–150° C. (decomposition)

Example 5

3-benzylaminopiperidine-2,6-dione

A) A solution of 0.50 g 3-aminopiperidine-2,6-dione (K. Fickentscher, Arch. Pharm. 1974, 307, 840–844), 1.5 ml triethylamine and 0.4 ml benzyl bromide was stirred for 20 h at 20° C. It was then evaporated, the residue taken up in 50 ml aqueous potassium carbonate solution (10% K$_2$CO$_3$) and the solution extracted twice with 40 ml ethyl acetate each. The organic phases were washed with 50 ml each of distilled water and saturated sodium chloride solution, dried over sodium sulfate and evaporated in vacuo. The residue was purified by flash chromatography on silica gel with a mixture of ethyl acetate/cyclohexane (2/1) containing 1% triethylamine as eluent, whereby 0.21 g (26% of theoretical) of the title compound was obtained as viscous oil.

The title compound could also be obtained in the form of the hydrobromide as pure S enantiomer in the following way:

B) Step 1:

(2S)-(N-benzyl-N-benzyloxycarbonylamino)-4-carbamoyl butanoic acid 0.6 ml benzyl chloroformate were added dropwise to 0.95 g (2S)-benzylamino-4-carbamoyl butanoic acid (E. Davidov et al., Isr. J. Chem. 1969, 7, 487–489) dissolved in 4 ml 2 M aqueous sodium hydroxide and 8 ml 1 M sodium hydrogen carbonate solution, over 2.5 h at 20° C. whilst being stirred. The mixture was then extracted twice with 20 ml diethyl ether each. The aqueous phase was acidified with conc. hydrochloric acid to pH 2–3 and extracted twice with 30 ml ethyl acetate each. The extracts were washed with distilled water, dried over sodium sulfate and evaporated in vacuo. After adding diethyl ether to the oily residue, 0.55 g (37% of theoretical) of the title compound were obtained in the form of colorless crystals, which melted at 98–99° C.

Step 2:

(3S)—(N-butyl-N-benzyloxycarbonylamino) piperidine-2,6-dione

A solution of 0.162 g N,N'-carbonyl diimidazole in 3 ml dry tetrahydrofuran was dripped into a solution of 0.37 g of the product from step 1 in 2.5 ml dry tetrahydrofuran. It was refluxed for 3.5 h then stirred for a further 3 h at 20° C. The oil remaining after evaporation of the solvent in vacuo was dissolved in ethyl acetate and the solution washed successively with 20 ml each of 1 M aqueous sodium hydrogen carbonate solution, saturated sodium chloride solution and distilled water. It was then dried over sodium sulfate and evaporated in vacuo. 0.23 g (65% of theoretical) of the title compound remained in the form of crystals, which melted at 51–52° C.

Step 3:

(3S)-benzylaminopiperidine-2,6-dione; hydrobromide

The solution of 0.15 g of the product from step 2 in 3 ml of a solution of hydrogen bromide in acetic acid (33% HBr) was stirred for 1 h at 20° C. The reaction mixture was then poured onto 50 ml diethyl ether. The precipitate that was formed was separated off, washed with diethyl ether and dried in vacuo. 0.08 g (63% of theoretical) of the title compound remained in the form of crystals, which melted at 228-230° C. with decomposition.

$^1$H-NMR (DMSO-$d_6$): 2.01–2.43 (m, 2H); 2.60–2.80 (m, 2H); 4.20–4.45 (m, 3H); 7.40–7.60 (m, 5H).

Example 6

6.1 2-[(3S)-(2,6-dioxopiperidin-3-ylamino)methyl]benzoic acid, hydrobromide

Step 1:

2-[(1S)-(3-carbamoyl-1-carboxypropylamino) methyl]benzoic acid

A suspension of 1.65 g 2-formylbenzoic acid in 5 ml ethanol and 5 ml 2 M sodium hydroxide solution was added to a solution of 1.46 g L-glutamine in 5 ml of a 2 M aqueous sodium hydroxide solution. After stirring for 1 h at 20° C., the mixture was cooled to 0° C. and 0.25 g sodium borohydride were added in portions over 15 min with vigorous stirring. After 90 min a further 0.33 g 2-formyl benzoic acid and 0.05 g sodium borohydride were added. After stirring for 16 h at 20° C., the reaction mixture was acidified with conc. hydrochloric acid to pH 2 and cooled to 0° C. The precipitate formed was separated off, washed with acetone and dried in vacuo. 0.87 g (31% of theoretical) of the title compound remained in the form of crystals, which melted at 132–133° C.

Step 2:

2-{(1S)-[N-benzyloxycarbonyl-N-(3-carbamoyl-1-carboxypropyl)amino]methyl}benzoic acid Using the procedure described in Example 5 B, step 1, the title compound was obtained in the same way from the product from step 1 in the form of crystals, which melted with decomposition at 103–104° C.

Step 3:

2-{(3S)-[N-benzyloxycarbonyl-N-(2,6-dioxopiperidin-3-yl)amino]methyl}benzoic acid Using the procedure described in Example 5 B, step 2, the title compound was obtained in the same way from the product from step 2 in the form of crystals, which melted at 71–73° C.

Step 4:

2-[(3S)-(2,6-dioxopiperidin-3-ylamino)methyl]benzoic acid, hydrobromide

Using the procedure described in Example 5B, step 3, the title compound was obtained in the same way from the product from step 3 in the form of colorless crystals, which melted at 158–161° C.

$^1$H-NMR (DMSO-$d_6$): 2.00–2.25 (m, 1H); 2.35–2.95 (m, 1H); 2.60–2.80 (m, 2H); 4.35–4.50 (m, 1H); 4.50–4.70 (m, 2H); 7.50–7.75 (m, 3H); 8.00–8.10 (m, 1H).

6.2 2-[(3R)-(2,6-dioxopiperidin-3-ylamino)methyl]benzoic acid; hydrobromide

Replacing L- by D-glutamine in Example 6.1, step 1, and using the procedure described in Example 6.1, the title compound was obtained in the same way in the form of crystals, which melted at 148–152° C.

Example 7

2-[(3S)-(2,6-dioxopiperidin-3-ylamino)methyl]-N,N-diethylbenzamide; hydrobromide Step 1:

(3S)-[N-(2-diethylcarbamoylbenzyl)-N-benzyloxycarbonyl]aminopiperidine-2,6-dione A solution of 1.00 g of the product from Example 6.1, step 3, 0.27 g N-methyl morpholine and 0.46 g 2-chloro-4,6-dimethoxy-1,3,5-triazine in 7 ml dry tetrahydrofuran was stirred for 1 h at 20° C. After adding 0.19 g diethylamine, stirring was continued for a further 7 h. The solution was then diluted with chloroform to a volume of 50 ml and washed successively with 25 ml 0.05 N hydrochloric acid, 25 ml 1 M aqueous sodium hydrogen carbonate solution and saturated sodium chloride solution. The organic phase was dried over sodium sulfate and evaporated in vacuo. After purifying the residue by flash chromatography on silica gel with ethyl acetate/cyclohexane (9/1) as eluent, 0.36 g (32% of theoretical) of the title compound were obtained in the form of crystals, which melted at 65–66° C.

Step 2:

2-[(3S)-(2,6-dioxopiperidin-3-ylamino) methyl]-N, N-diethylbenzamide; hydrobromide 0.30 g of the product from step 1 were reacted as described in Example 5B, step 3 with 3 ml of a solution of hydrogen bromide in acetic acid (33% HBr). After working up and purification by recrystallisation from methanol/diethyl ether, 0.175 g (66% of theoretical) of the title compound were obtained in the form of crystals, which melted at 119–120° C.

$^1$H-NMR (DMSO-$d_6$): 1.06 (t, J=7.5 Hz, 3H); 1.21 (t, J=6.9 Hz, 3H); 2.04–2.24 (m, 1H); 2.28–2.46 (m, 2H); 2.58–2.80 (m, 2H); 3.19 (dd, 2H); 3.51 (dd, 2H); 4.24 (s, 2H); 4.25–4.40 (m, 1H); 7.44 (d, 1H); 7.48–7.66 (m, 2H); 7.72 (d, 1H).

Example 8

By replacing diethylamine in Example 7, step 1, by other amines, ammonia or hydrazine and using the additional procedure described in Example 7, the following were obtained in the same way:

8.1: (3S)-[2-morpholine-4-carbonyl)benzylamino] piperidine-2,6-dione; hydrobromide
Melting point: 133–135° C.

8.2: {2-[(3S)-(2,6-dioxopiperidin-3-ylamino)methyl] benzoylamino}methyl acetate; hydrobromide
Melting point: 121–123° C.

8.3: 2-[(3S)-(2,6-dioxopiperidin-3-ylamino)methyl] benzamide; hydrobromide

Melting point: 155–156° C. (decomposition)

8.4: 2-[(3S)-(2,6-dioxopiperidin-3-ylamino)methyl]-N-ethyl benzamide; hydrobromide
Melting point: 144–146° C.

8.5: (3S)-[2-pyrrolidine-1-carbonyl)benzylamino]piperidin-2,6-dione; hydrobromide
Melting point: 136–138° C.

8.6: 2-[(3S)-(2,6-dioxopiperidin-3-ylamino)methyl]benzoic acid hydrazide; hydrobromide
Melting point: 241–242° C.

8.7: 2-[(3S)-(2,6-dioxopiperidin-3-ylamino)methyl]-N-phenylbenzamide; hydrobromide
Melting point: 136–138° C.

8.8: (2R)-{(3S)-2-[(2,6-dioxopiperidin-3-ylamino)methyl]benzoylamino}methyl phenylacetate; hydrobromide
Melting point: 149–151° C.

8.9: (2S)-{(3S)-2-[(2,6-dioxopiperidin-3-ylamino)methyl]benzoylamino}methyl phenylacetate; hydrobromide
Melting point: 181–182° C.

8.10: 2-[(3R)-(2,6-dioxopiperidin-3-ylamino)methyl]-N-phenyl benzamide; hydrobromide
Melting point: 168–171° C.

8.11: 2-[(3R)-(2,6-dioxopiperidin-3-ylamino)methyl]-N,N-diethyl benzamide; hydrobromide
Melting point: 128–132° C.

8.12: 2-[(3R)-(2,6-dioxopiperidin-3-ylamino)methyl] benzamide; hydrobromide
Melting point: 232–233° C.

Example 9

9.1: 2-[(3S)-(2,6-dioxopiperidin-3-ylamino)methyl]methyl benzoate; hydrobromide
Step 1:

2-{(3S)-[N-benzyloxycarbonyl-N-(2,6-dioxopiperidin-3-yl)amino]-methyl}methyl benzoate A mixture consisting of 0.60 g of the product from Example 6.1, step 3, and 0.25 g N,N'-carbonyl diimidazole in 5 ml dry tetrahydrofuran was stirred for 1.5 h at 20° C. 64 µl methanol were then added and stirring was continued for a further 40 h at 20° C. After evaporating off the solvent in vacuo the residue was taken up in 80 ml chloroform and the solution washed with 1 M sodium hydrogen carbonate solution and distilled water. It was dried over sodium sulfate and evaporated in vacuo. After purification of the residue by column chromatography on silica gel with chloroform/acetone (94/6) as eluent, 0.32 g (51% of theoretical) of the title compound were obtained as a viscous oil.

Step 2:

2-[(3S)-(2,6-dioxopiperidin-3-ylamino)methyl] methyl benzoate; hydrobromide

By removing the benzyloxycarbonyl protective group in the product from step 1 using the procedure described in Example 5B, step 3, the title compound was obtained in the same way in the form of crystals, which melted at 187° C.

$^1$H-NMR (DMSO-$d_6$): 2.07–2.30 (m, 1H); 2.30–2.48 (m, 1H); 2.60–2.85 (m, 2H); 3.90 (s, 3H); 4.40–4.70 (m, 3H); 7.58–7.78 (m, 3H); 8.05 (d, J=8 Hz, 1H).

9.2: 2-[(3S)-(2,6-dioxopiperidin-3-ylamino)methyl]benzyl benzoate; hydrobromide

By replacing methanol with benzyl alcohol in Example 9.1 and using the procedure described therein, the title compound was obtained in the same way in the form of white crystals, which melted at 175–177° C.

Example 10

3-phenylaminomethyl piperidine-2,6-dione 30 ml absolute triethylamine and 2.75 ml freshly distilled aniline were added to a solution of 1.25 g 3-methylene piperidine-2,6-dione (M. J. Wanner and G. -J. Koomen, Tetrahedron Lett. 1992, 33, 1513–1516) in 100 ml acetonitrile and the mixture was stirred for 16 h at 80° C.

After cooling, 10 g silica gel were added and the mixture was evaporated in vacuo. The residue was purified by flash chromatography on silica gel with tert-butyl methyl ether/cyclohexane (2/1) as eluent. 1.87 g (86% of theoretical) of the title compound were obtained in the form of crystals, which melted at 137° C.

$^1$H-NMR (CDCl$_3$): 1.84–1.99 (m, 1H); 2.08–2.17 (m, 1H); 2.49–2.64 (m, 1H); 2.73–2.83 (m, 2H); 3.41–3.50 (m, 1H); 3.60–3.70 (m, 1H); 6.64–6.80 (m, 3H); 7.17–7.29 (m, 2H).

Example 11

By replacing aniline in Example 10 by other amines and using the procedure therein described, whereby optionally the mixture of toluene/diisopropyl ethylamine was also used instead of the solvent system acetonitrile/triethylamine at a reaction temperature of 110° C., the following compounds could be obtained in the same way:

11.1: 3-[(4-bromophenylamino)methyl]piperidine-2,6-dione
Melting point: 149–150° C.

11.2: 3-[(3-trifluoromethyl phenylamino)methyl]piperidine-2,6-dione
Melting point: 135–138° C.

11.3: 3-(naphth-1-ylaminomethyl) piperidine-2,6-dione
Melting point: 145–148° C.

11.4: 3-(biphenyl-4-ylaminomethyl) piperidine-2,6-dione
Melting point: 135–138° C.

11.5: 3-[(3-methoxyphenylamino)methyl]piperidine-2,6-dione
Viscous 11.6: 3-[(4-trityl phenylamino)methyl]piperidine-2,6-dione
Melting point: 221–225° C.

11.7: 3-[(2,6-dioxopiperidin-3-ylmethyl)amino]ethyl benzoate
Viscous 11.8: 3-(benzylaminomethyl) piperidine-2,6-dione
Viscous 11.9: 3-[(3-acetyl phenylamino)methyl]piperidine-2,6-dione
Melting point: 129–132° C.

11.10: 3-[(N-methyl-N-phenylamino)methyl]piperidine-2,6-dione
Melting point: 132–134° C.

11.11: 3-{[(naphth-1-ylmethyl)amino]methyl}piperidine-2,6-dione
Viscous 11.12: 3-[(2-methoxyphenylamino)methyl]piperidine-2,6-dione
Viscous 11.13: 3-[(4-methoxyphenylamino)methyl]piperidine-2,6-dione
Melting point: 131–134° C.

11.14: (2S)-[(2,6-dioxopiperidin-3-ylmethyl)amino]-3-methyl phenylpropionate
Viscous 11.15: 2-[(2,6-dioxopiperidin-3-ylmethyl)amino]benzamide
Melting point: 203–206° C.

11.16: 3-[(4-acetylphenylamino)methyl]piperidine-2,6-dione
Melting point: 160° C.

11.17: 3-[(3-benzoyl phenylamino)methyl]piperidine-2,6-dione
Melting point: 152–158° C.

11.18: 4-[(2,6-dioxopiperidin-3-ylmethyl)amino]methyl benzoate
Melting point: 142–144° C.

Example 12

3-[(2-hydroxymethyl phenylamino)methyl] piperidine-2,6-dione

Step 1:

3-{[2-tert-butyl dimethyl silanyloxymethyl) phenylamino]methyl}piperidine-2,6-dione By replacing aniline in Example 10 by 2-(tert-butyl dimethyl silanyloxymethyl) phenylamine and using the procedure therein described, the title compound was obtained in the form of white crystals, which melted at 85–87° C.

Step 2:

3-[(2-hydroxymethyl phenylamino)methyl] piperidine-2,6-dione 5 ml of a 1 M solution of tetrabutyl ammonium fluoride trihydrate in tetrahydrofuran were added to a solution of 0.20 g of the product from step 1 in 5 ml tetrahydrofuran. It was stirred for 3 h at 20° C., evaporated in vacuo and the residue was purified by flash chromatography on silica gel with ethyl acetate as eluent. 0.12 g (85% of theoretical) of the title compound were obtained in the form of a yellowish oil.

Example 13

By replacing aniline in Example 10 by thiophenols or mercaptans and using the procedure therein described, the following were obtained in the same way:

13.1: 3-phenylsulfanylmethyl piperidine-2,6-dione
Melting point: 98° C.

13.2: 3-phenethylsulfanylmethyl piperidine-2,6-dione
Melting point: 78° C.

13.3: 2-(2,6-dioxopiperidin-3-ylmethyl)sulfanyl) methyl benzoate
Melting point: 142–144° C.

13.4: 3-benzylsulfanylmethyl piperidine-2,6-dione
Melting point: 105–107° C.

13.5: 3-(3-aminophenylsulfanylmethyl) piperidine-2,6-dione
Melting point: 133–135° C.

13.6: 5-(2,6-dioxopiperidin-3-ylmethylsulfanyl)-6-nitro methylbenzoate
Melting point: 147–150° C.

Example 14

2-amino-5-(2,6-dioxopiperidin-3-ylmethylsulfanyl) Methyl Benzoate

The title compound was obtained in the same way by catalytic hydrogenation of the product from Example 13.6 over palladium on activated carbon (10% Pd) under the conditions described in Example 3.
Melting point: 164–167° C.

Example 15

3-phenylsulfanylmethyl-1-piperidin-1-ylmethyl piperidine-2,6-dione 0.52 ml aqueous formaldehyde solution (35%) and 0.43 ml piperidine were added to a solution of 1.20 g of the product from Example 13.1 in 30 ml ethanol. After being refluxed for 1 hour, the mixture was evaporated in vacuo. The residue was taken up in ethyl acetate and n-hexane was added to the solution until precipitation. The crystals were separated off and dried in vacuo. 1.23 g (74% of theoretical) of the title compound were obtained, which displayed a melting point of 63–66° C.

$^1$H-NMR (DMSO-d$_6$): 1.37–1.47 (m, 6H), 1.72–1.88 (m, 1H), 2.08–2.16 (m, 1H), 2.21–2.33 (m, 4H), 2.49–2.57 (m, 1H), 2.70–2.82 (m, 1H), 3.07–3.18 (m, 1H), 3.28–3.33 (m, 1H), 3.47–3.56 (m, 1H), 4.56–4.69 (m, 2H), 7.17–7.25 (m, 1H), 7.28–7.39 (m, 4H).

Example 16

N-{2-[2,6-dioxopiperidin-3-ylamino)methyl] phenyl}acetamide; hydrobromide

Step 1:

2[(2-acetyl aminobenzyl) benzyloxycarbonylamino]-4-carbamoyl Butanoic Acid 1.20 g N-(2-formyl phenyl) acetamide, dissolved in 10 ml methanol and 3.7 ml 1 N sodium hydroxide solution, were added to a solution of 0.98 g L-glutamine in 3.4 ml 2N sodium hydroxide solution, stirred for 30 minutes at 20° C. and cooled to 0° C. 0.31 g sodium borohydride were then added in portions with stirring over 30 minutes. Stirring was continued for 16 hours at 0 to 5° C. and 14.2 ml of a 1N aqueous sodium hydrogen carbonate solution were then added. A solution of 1.4 ml benzyl oxycarbonyl chloride in 1.1 ml tetrahydrofuran and 2.5 ml 4N sodium hydroxide solution were then simultaneously added dropwise over one hour. Stirring was continued for 2 hours at 20° C. The neutral reaction solution was extracted three times with diethyl ether and the aqueous phase then adjusted to pH 1 to 2 with 1N hydrochloric acid. It was then extracted three times with 20 ml ethyl acetate. The combined organic phases were washed with 20 ml saturated sodium chloride solution, dried over sodium sulfate and evaporated in vacuo. 0.93 g of the unpurified title compound were obtained, which were then reacted further.

Step 2:

(2-acetylaminobenzyl)-(2,6-dioxopiperidin-3-yl) Benzyl Carbamate

A solution of 0.36 g carbonyl diimidazole in 3 ml absolute tetrahydrofuran was added to a solution of 0.90 g of the product from step 1 in 6 ml anhydrous tetrahydrofuran. The mixture was refluxed for 4 hours. After evaporation of the solvent in vacuo, the residue was taken up in 50 ml distilled water and extracted three times with 50 ml ethyl acetate. The extracts were first washed three times with 50 ml water, then with saturated sodium chloride solution, dried over sodium sulfate and evaporated in vacuo. 0.25 g (11% of theoretical, relative to the L-glutamine used in step 1) of the title compound were obtained by flash chromatography on silica gel with ethyl acetate/cyclohexane (2/1).

Step 3:

N-{2-[(2,6-dioxopiperidin-3-ylamino)methyl] phenyl}acetamide; hydrobromide 1 ml of a solution of hydrogen bromide in glacial acetic acid (33% HBr) was added to a suspension of 0.20 g of the product from step 2 in 1 ml glacial acetic acid. The mixture was stirred for 1 hour at 20° C. and then poured into 100 ml diethyl ether. After cooling to 0 to 5° C. the solid that had formed was separated off, washed with diethyl ether and dried in vacuo. After reprecipitation from methanol/diethyl ether, 0.09 g (50% of theoretical) of the title compound were obtained.

Melting point: 152–156° C. $^1$H-NMR (DMSO-$d_6$): 2.05–2.22 (m, 1H); 2.13 (s, 3H); 2.35–2.74 (m, 1H); 2.69–2.74 (m, 2H); 4.26 (s, 2H); 4.43 (d, 1H); 7.33–7.60 (m, 4H); 9.88 (s, 1H); 11.41 (s, 1H).

Example 17

N-{2-[(2,6-dioxopiperidin-3-ylamino)methyl]phenyl}Formamide; hydrobromide

By replacing the acetamide derivative used in Example 16, step 1, with N-(2-formyl phenyl) formamide and using the procedure described in steps 1 to 3, the title compound was obtained in the same way.

Melting point: 169–174° C.

Example 18

3-(2,6-dioxopiperidin-3-yl methyl sulfanyl)-6-nitro Methylbenzoate

The title compound was produced using the procedure described in Example 10, by replacing the aniline with the corresponding mercaptan (formula X with $R^1$=COOCH$_3$ in the 3 position and $R^2$=NO$_2$ in the 4 position).

Melting point: 147–150° C.

Example 19

2-amino-5-(2,6-dioxopiperidin-3-yl methyl sulfanyl) methyl benzoate

The title compound was obtained in the same way by catalytic hydrogenation of the product from Example 18 over palladium on activated carbon (10% Pd) under the conditions described in Example 3.

Melting point: 164–167° C.

Stimulation of Human Monocytes with Lipopolysaccharide for Secretion of IL-12

Human monocytes were isolated from peripheral blood mononuclear cells (PBMC) obtained by means of a Ficoll density-gradient centrifugation of heparinized whole blood. To this end, the PBMC were incubated with a monoclonal antibody directed against the monocyte-specific surface molecule CD14 and to which superparamagnetic microbeads (Miltenyi Biotech, Bergisch Gladbach) are coupled. In order for the marked monocytes to be positively selected from the mixture of cells in the PBMC, the total cell suspension was transferred to a column with a ferromagnetic carrier matrix and the column placed in a magnetic field. This caused the cells loaded with microbeads to be bonded to the carrier matrix, whilst unmarked cells passed through the column and were discarded. After removing the matrix from the magnetic field, the antibody-loaded cells were eluted by rinsing the now demagnetised column with buffer. The purity of this CD 14-positive monocyte population thus obtained was around 95 to 98%. These monocytes were incubated in a density of $10^6$ cells/ml culture medium (RPMI, supplemented with 10% fetal calf serum) with the test substances dissolved in DMSO for one hour at 37° C. and 5% CO$_2$.20 μg/ml LPS from E. coli were then added. After 24 hours, cell-free culture supernatants were taken and tested for their IL-12 content.

The concentration of IL-12 in the cell culture supernatants was determined by means of sandwich ELISA using two anti-IL-12 monoclonal antibodies (Biosource Europe, Fleurus, Belgium). A reference standard curve with human IL-12 was included. The detection limit of the IL-12 ELISA was 10 pg/ml.

TABLE 1

Influence of the test substances on IL-12 production by LPS-activated monocytes.

| | Inhibition of IL-12 production | |
|---|---|---|
| Example no. | Maximum (%) | IC50 (μg/ml) |
| 6.1 | 85 | 1.0 |
| 6.2 | 75 | 1.0 |
| 9.1 | 90 | 0.1 |
| 9.2 | 82 | 1.5 |
| 8.3 | 90 | 0.15 |
| 8.12 | 84 | 1.0 |
| 7 | 90 | 1.5 |
| 8.11 | 90 | 0.2 |
| 8.1 | 90 | 1.8 |
| 8.5 | 80 | 2.0 |
| 8.4 | 80 | 0.9 |
| 8.7 | 55 | 0.7 |
| 8.10 | 50 | — |
| 8.6 | 90 | 0.04 |
| 8.2 | 70 | 1.8 |
| 13.3 | 50 | 6.0 |
| 16 | 95 | 3.0 |
| 17 | 98 | 0.02 |
| 18 | 57 | 3.0 |
| 19 | 66 | 5.0 |

The results set out in Table 1 show that the substituted glutarimides have an immunomodulatory action. They exert a potent inhibitory effect on the synthesis of IL-12 by LPS-activated monocytes.

The foregoing description and examples have been set forth merely to illustrate invention and are not intended to be limiting. Since modifications of the described embodiments incorporating the spirit and substance of the invention may occur to persons skilled in the art, the invention should be construed broadly to include all variations falling within the appended claims and equivalents thereof.

We claim:

1. A substituted glutarimide compound of formula I

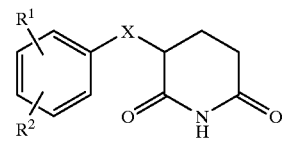

wherein

X is CH$_2$—NH or S—CH$_2$, $R^1$ is a carboxyl group; an ester group having the formula COOR$^5$ in which R$^5$ is a C$_1$–C$_6$ straight-chain or branched alkyl group or a benzyl group; or an amide group having the formula CONR$^6$R$^7$, in which
R$^6$ and R$^7$ are the same or different and represent a hydrogen; a C$_1$–C$_6$ straight-chain or branched alkyl group optionally substituted with a COOR$^5$ group or a phenyl group or both; or a phenyl group;
or R$^6$ and R$^7$ taken together with the N atom represent a hydrazide group; a pyrrolidine; a piperidine or a morpholine ring; or an amino group substituted with a CH(=O) or COR$^5$; and R² is a hydrogen, an amino or a nitro group, or a salt thereof with a physiologically compatible acid.

2. An enantiomer, or a salt thereof with a physiologically compatible acid, of a compound according to claim 1.

3. A mixture of enantiomers, or salts thereof with a physiologically compatible acid, of at least a compound according to claim 1.

4. A racemate, or a salt thereof with a physiologically compatible acid, of a compound according to claim 1.

5. A diastereomer, or mixture of diastereomers thereof, or a salt thereof with a physiologically compatible acid, of a compound according to claim 1.

6. A compound according to claim 1, selected from the group consisting of:

2-[(3S)-(2,6-dioxopiperidin-3-ylamino)methyl]benzoic acid,

2-[(3R)-(2,6-dioxopiperidin-3-ylamino)methyl]benzoic acid,

2-[(3S)-(2,6-dioxopiperidin-3-ylamino) methyl]-N,N-diethylbenzamide, (3S)-[2-morpholine-4-carbonyl)benzylamino]piperidine-2,6-dione, {2-[(3S)-(2,6-dioxopiperidin-3-ylamino)methyl]benzoylamino}methyl acetate, 2-[(3S)-(2,6-dioxopiperidin-3-ylamino)methyl]benzamide, 2-[(3S)-(2,6-dioxopiperidin-3-ylamino)methyl]-N-ethyl benzamide, (3S)-[2-pyrrolidine-1-carbonyl)benzylamino]piperidine-2,6-dione, 2-[(3S)-(2,6-dioxopiperidin-3-ylamino)methyl]benzoic acid hydrazide, 2-[(3S)-(2,6-dioxopiperidin-3-ylamino)methyl]-N-phenyl benzamide, 2-[(3R)-(2,6-dioxopiperidin-3-ylamino)methyl]-N-phenyl benzamide, 2-[(3R)-(2,6-dioxopiperidin-3-ylamino)methyl]-N,N-diethyl benzamide, 2-[(3R)-(2,6-dioxopiperidin-3-ylamino)methyl] benzamide, 2-[(3S)-(2,6-dioxopiperidin-3-ylamino)methyl]methyl benzoate, 2-[(3S)-(2,6-dioxopiperidin-3-ylamino)methyl]benzyl benzoate, 2-(2,6-dioxopiperidin-3-yl methyl sulfanyl) methyl benzoate, N-{2-[2,6-dioxopiperidin-3-ylamino)methyl]phenyl}acetamide, N-{2-[2,6-dioxopiperidin-3-ylamino)methyl]phenyl}formamide, 3-(2,6-dioxopiperidin-3-yl methyl sulfanyl)-6-nitro methylbenzoate, and 2-amino-5-(2,6-dioxopiperidin-3-yl methyl sulfanyl) methyl benzoate.

7. A pharmaceutical composition comprising as an active agent at least one compound according to claim 1, and a pharmaceutically acceptable excipient.

8. A method for modulating immune action in a mammal in need thereof, comprising administering to the mammal an effective immunomodulatory amount of a compound of claim 1.

9. A method according to claim 8, wherein the mammal is a human.

10. A method for the production of a substituted glutarimide compound according to claim 1, the method comprising cyclizing a glutaric acid derivative of formula II,

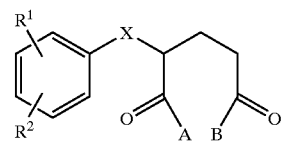

wherein X, R¹ and R² are as defined in formula I; and A is OH, and B is NH₂ or NHOH; or A is NH₂ or NHOH, and B is OH, in the presence of an activating reagent.

11. A method according to claim 10, wherein the activating agent is carbonyl diimidazole.

12. A method according to claim 10, wherein X is CH₂—NH, and wherein cyclization is performed with the —NH group of X protected by a protective group, which protective group is removed after cyclization.

13. A method according to claim 12, wherein the protective group is a benzyloxycarbonyl group.

* * * * *